US006723867B1

(12) United States Patent
Huebner et al.

(10) Patent No.: US 6,723,867 B1
(45) Date of Patent: Apr. 20, 2004

(54) BRANCHED, SUBSTANTIALLY UNSATURATED FATTY ALCOHOL SULFATES

(75) Inventors: Norbert Huebner, Langenfeld (DE); Hans-Christian Raths, Monheim (DE); Alfred Westfechtel, Hilden (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 36 days.

(21) Appl. No.: 10/049,960

(22) PCT Filed: Aug. 11, 2000

(86) PCT No.: PCT/EP00/07849

§ 371 (c)(1),
(2), (4) Date: Jun. 19, 2002

(87) PCT Pub. No.: WO01/14325

PCT Pub. Date: Mar. 1, 2001

(30) Foreign Application Priority Data

Aug. 20, 1999 (DE) .................. 199 39 565

(51) Int. Cl.$^7$ ............................ C07C 305/14
(52) U.S. Cl. ................. 558/20; 568/864
(58) Field of Search ............. 558/20; 568/864

(56) References Cited

U.S. PATENT DOCUMENTS

| | | |
|---|---|---|
| 3,193,586 A | 7/1965 | Rittmeister |
| 3,729,520 A | 4/1973 | Rutzen et al. |
| 3,966,629 A | 6/1976 | Dumbrell |
| 4,062,647 A | 12/1977 | Storm et al. |
| 4,172,887 A | 10/1979 | Vanlerberghe et al. |
| 4,321,157 A | 3/1982 | Harris et al. |
| 4,664,839 A | 5/1987 | Rieck |
| 4,737,306 A | 4/1988 | Wichelhaus et al. |
| 4,816,553 A | 3/1989 | Baur et al. |
| 5,008,032 A | 4/1991 | Diessel et al. |
| 5,356,607 A | 10/1994 | Just |
| 5,399,792 A | 3/1995 | Demmering |
| 5,580,941 A | 12/1996 | Krause et al. |
| 5,672,781 A | 9/1997 | Koehler et al. |
| 5,705,169 A | 1/1998 | Stein et al. |
| 5,730,960 A | 3/1998 | Stein et al. |
| 5,830,956 A | 11/1998 | Stockhausen et al. |
| 5,917,097 A | 6/1999 | Koehler et al. |
| 5,945,091 A | 8/1999 | Habeck et al. |
| 6,193,960 B1 | 2/2001 | Metzger et al. |

FOREIGN PATENT DOCUMENTS

| | | |
|---|---|---|
| DE | 11 65 574 A | 3/1964 |
| DE | 2 334 899 A | 1/1974 |
| DE | 20 24 051 C3 | 10/1979 |
| DE | 35 26 405 A1 | 2/1987 |
| DE | 42 21 381 C1 | 2/1994 |
| DE | 43 00 772 A1 | 7/1994 |
| DE | 43 35 781 C2 | 2/1998 |
| DE | 197 12 033 A1 | 9/1998 |
| EP | 0 026 529 A1 | 4/1981 |
| EP | 0 028 432 A1 | 5/1981 |
| EP | 0 164 514 A1 | 12/1985 |
| EP | 0 280 223 A2 | 8/1988 |
| EP | 0 367 049 B1 | 2/1994 |
| EP | 0 602 108 B1 | 1/1996 |
| EP | 0 693 471 B1 | 1/1998 |
| EP | 0 694 521 B1 | 1/1998 |
| EP | 0 818 450 A1 | 1/1998 |
| FR | 2 252 840 A | 8/1975 |
| GB | 962919 A | 7/1964 |
| GB | 1 333 475 A | 10/1973 |
| GB | 1 400 898 A | 7/1975 |
| JP | 09169720 A | 6/1995 |
| WO | 91/08171 A1 | 6/1991 |
| WO | 96/02619 A1 | 2/1996 |
| WO | 98/42646 A1 | 10/1998 |

OTHER PUBLICATIONS

T. Zimaity et al., J. Amer. Oil Chem. Soc., vol. 48, No. 11, 1971, pp. 665–667, XP000979317.
H. Möhring et al., Fat Sci. Technol., vol. 92, No. 7, 1990, pp. 255–259, XP000982075.
Behr et al., "Katalytische Oligomerisierung von Fettstoffen", Fat. Sci. Technol. vol. 93, (1991), pp. 340–345.
Möhring et al., "Produkte der Dimerisierung ungesättigter Fettsäuren VII: Kinetische Untersuchung der Mono–und Dimeren, die bel der Dimerisierung von Olsaure entstehen", Fat. Sci. Technol., vol. 94, (1992), pp. 41–46.
Möhring et al., "Produkte der Dimerisierung ungesättigter Fettsäuren VIII: Uber die Zusammensetzung der Fraktion der "Intermediates" bei der Fettsäuredimerisierung" Fat. Sci. Technol., vol. 94, (1992), pp. 241–245.
Falbe (Editor), "Surfactants in Consumer Products", Springer–Verlag, Berlin–Heidelberg, (1987), pp. 61–63.
Todd et al., "Volatile silicone fluids for cosmetic formulations", Cosmetics and Toiletries. vol. 91, (Jan., 1976), pp. 29–32.
Lochhead et al., "Encyclopedia of Polymers and Thickeners for Cosmetics", Cosmetics and Toiletries, vol. 108, (May, 1993), pp. 95–114, 116–124, 127–130, 132–135.
Finkel, "Formullerung kosmetischer Sonnenschutzmittel", SÖFW–Journal, vol. 122, (1996), pp. 543–546 & 548.
"Kosmetische Färbemittel", Farbstoffkommission der Deutschen Forschungsgemeinschaft, Verlag Chemie, Weinheim (1984), pp. 81–106.

*Primary Examiner*—Joseph K. McKane
*Assistant Examiner*—Kamal Saeed
(74) *Attorney, Agent, or Firm*—John E. Drach

(57) ABSTRACT

Branched, substantially unsaturated fatty alcohol sulfates are produced by a process which comprises the steps of: (a) dimerizing unsaturated $C_{16-22}$ fatty acid to form a dimer fraction and a monomer fraction comprised of branched, substantially unsaturated fatty acids and straight chain saturated fatty acids, (b) removing the monomer fraction from the dimerization step, (c) converting the branched, substantially unsaturated fatty acids from step (b) into the corresponding fatty acid methyl esters, (d) hydrogenating the branched, substantially unsaturated fatty acid methyl esters with the double bonds intact to form the corresponding branched, substantially unsaturated fatty alcohols and (e) sulfating and neutralizing the branched, substantially unsaturated fatty alcohols. The fatty alcohol sulfates thus produced exhibit improved performance properties and greater oxidative stability than standard unsaturated fatty alcohol sulfates.

6 Claims, No Drawings

BRANCHED, SUBSTANTIALLY UNSATURATED FATTY ALCOHOL SULFATES

BACKGROUND OF THE INVENTION

This invention relates generally to anionic surfactants and, more particularly, to substantially unsaturated fatty alcohol sulfates which, through the presence of branches in the hydrocarbon chain, are distinguished from linear homologs by significantly improved properties, to a process for their production and to their use for the production of surface-active compositions.

PRIOR ART

Sulfates of unsaturated fatty alcohols, which are essentially obtained by sulfation and subsequent neutralization of the corresponding tallow-based alkenols, are important raw materials for the production of both cosmetic preparations and laundry detergents, dishwashing detergents and cleaning products. The favorable properties of these substances are linked to the presence of the double bond in the molecule which also presents problems because the unsaturated fatty alcohol ether sulfates readily fall victim to autoxidation which is which is associated with discoloration and unwanted chemical changes (for example formation of peroxides and hydroperoxides).

Accordingly, it is clear that there is a need on the market for unsaturated fatty alcohol sulfates with improved oxidation stability or suitable substitutes which possess at least equivalent performance properties. However, more or less pure isostearyl alcohol sulfates have hitherto been the only alternatives to unsaturated fatty alcohol sulfates. To produce these more or less pure isostearyl alcohol sulfates, however, oleic acid first has to be dimerized, the fraction of monomeric branched fatty acids separated off, hydrogenated and subjected to fractional crystallization, the liquid fraction accumulating, which is rich in isostearic acid, has to be removed and esterified with methanol and the esters obtained subsequently hydrogenated to form the alcohols which, finally, are converted into the sulfates.

The process described above is technically complicated by the two hydrogenation steps and, in the isostearyl alcohol sulfates, provides substitutes which can only replace the unsaturated fatty alcohol sulfates to a limited extent. Accordingly, the problem addressed by the present invention was to provide unsaturated fatty alcohol sulfates which would be distinguished by improved performance properties and preferably by higher oxidation stability.

DESCRIPTION OF THE INVENTION

The present invention relates to branched, substantially unsaturated fatty alcohol sulfates which are obtainable by (a) dimerizing unsaturated $C_{16-22}$ fatty acids in known manner, (b) removing the monomer fraction accumulating in the dimerization step, (c) converting the branched, substantially unsaturated fatty acids present in this fraction into the corresponding fatty acid methyl esters, (d) hydrogenating the branched, substantially unsaturated fatty acid methyl esters with the double bonds intact to form the corresponding branched, substantially unsaturated fatty alcohols and (e) sulfating and neutralizing the branched, substantially unsaturated fatty alcohols in known manner.

It has surprisingly been found that the branched, substantially unsaturated fatty alcohol sulfates have distinctly improved autoxidation stability compared with linear homologs having the same chain length and the same iodine value. Further advantages include improved wetting behavior, quicker solubility in cold water and easier biodegradability.

The present invention also relates to a process for the production of branched, substantially unsaturated fatty alcohol sulfates in which (a) unsaturated $C_{16-22}$ fatty acids are dimerized in known manner, (b) the monomer fraction accumulating in the dimerization step is removed, (c) the branched, substantially unsaturated fatty adds present in this fraction are converted into the corresponding fatty add methyl esters, (d) the branched, substantially unsaturated fatty acid methyl esters are hydrogenated with the double bonds intact to form the corresponding branched, substantially unsaturated fatty alcohols which are then (e) sulfated and neutralized in known manner.

Production of the Fatty Alcohols

The dimerization of fatty acids and the recovery of monomer fatty acids from the dimers is sufficiently well-known from the prior art, cf. for example the overviews by A. Behr et al. [Fat Sci. Technol. 93, 340 (1991)] and by H. Möhring et al. [ibid. 94, 41 (1992) and 94, 241 (1992)]. The sequence of steps (a) to (d) gives branched, substantially unsaturated fatty alcohols with iodine values of 45 to 85 on the basis of dimerized, preferably monounsaturated $C_{16-22}$ fatty acids, i.e. oleic acid, elaidic acid, petroselic acid, gadoleic acid and erucic acid and mixtures thereof. This is without doubt entirely adequate for a number of applications. However, in cases where fatty compounds with a relatively high content of unsaturated compounds are required, it is advisable to subject the monomer fraction accumulating in the dimerization step to fractional crystallization and then to subject the liquid phase obtained to esterification, optionally after distillation. The fatty acid obtained and its methyl esters represent an already fairly pure isooleic acid or isooleic acid methyl ester with Iodine values of 75 to 95. In any event, it is advisable to subject the methyl esters and/or the fatty alcohols to distillation and/or fractional crystallization ("winterizing"). The esterification of the fatty acids with methanol is carried out by known methods and is intended to produce methyl esters which are comparatively easy to hydrogenate. Instead of the methyl esters, other lower alkyl esters, for example ethyl, propyl or butyl esters, may of course also be produced and subsequently hydrogenated. The choice of the alcohol is basically not critical and is solely determined by economic criteria and availability. Instead of the methyl or lower alkyl esters, it is also possible in principle directly to esterify the fatty acids, although this does involve the use of special catalysts which do not form salts with the acids. In addition, the reactor material has to be corrosion-resistant. The hydrogenation of the unsaturated methyl esters to form the corresponding alcohols may also be carried out in known manner. Corresponding processes and catalysts, particularly those based on copper and zinc, are disclosed for example in the following documents: DE 43 357 81 C1, EP 0 602 108 B1, U.S. Pat. No. 3,193,586 and U.S. Pat. No. 3,729,520 (Henkel); reference is expressly made to the disclosures of these documents.

Sulfation and Neutralization

The conversion of the fatty alcohols previously obtained into the sulfates may also be carried out in known manner. The attack of the sulfating agent may be directed both at the hydroxyl group and at the double bond. However, since the sulfation process takes place about 10 times more quickly than sulfonation, i.e. the addition of sulfur trioxide onto the double bond, at low temperatures of the order of 30° C., sulfates are predominantly obtained (i.e. to an extent of more than 90% by weight). The reaction of the branched, substantially unsaturated fatty alcohols, for example with gaseous sulfur trioxide, may be carried out in the same way as described for fatty acid lower alkyl esters in J. Falbe (ed.), "Surfactants in Consumer Products"; Springer Verlag, Berlin-Heidelberg, 1987, page 61, reactors operating on the falling-film principle being preferred. In this known process, the sulfur trioxide is diluted with an inert gas, preferably air or nitrogen, and used in the form of a gas mixture which contains the sulfonating agent in a concentration of 1 to 8% by volume and, more particularly, 2 to 5% by volume. The molar ratio of fatty alcohol to sulfating agent is 1:0.95 to 1:1.8, preferably from 1:1.0 to 1:1.6 and more preferably from 1:1.3 to 1:1.5. The sulfation reaction is generally carried out at temperatures of 25 to 90° C. and preferably at temperatures of 35 to 80° C. Instead of sulfur trioxide, chlorosulfonic acid or amidosulfonic acid may also be used as the sulfonating agent. The acidic sulfates accumulating during the reaction are stirred into aqueous bases, neutralized and adjusted to a pH value of 6.5 to 8.5. The neutralization step is carried out with bases selected from the group consisting of alkali metal hydroxides, such as sodium, potassium and lithium hydroxide, alkaline earth metal oxides and hydroxides, such as magnesium oxide, magnesium hydroxide, calcium oxide and calcium hydroxide, ammonia, mono-, di- and tri-$C_{2-4}$-alkanolamines, for example mono-, di- and triethanolamine, and primary, secondary or tertiary $C_{1-4}$ alkyl amines. The neutralization bases are preferably used in the form of 5 to 55% by weight aqueous solutions, 25 to 50% by weight aqueous sodium hydroxide solution being preferred. After neutralization, the sulfates obtainable by the process according to the invention are present as aqueous solutions with an active substance content of 20 to 80% by weight and preferably 30 to 50% by weight. After neutralization, the sulfates may be bleached in known manner by addition of hydrogen peroxide or sodium hypochlorite solution to achieve a further lightening in color desirable for many applications. 0.2 to 2% by weight of hydrogen peroxide—expressed as 100% by weight substance—or corresponding quantities of sodium hypochlorite, based on the solids content in the solution of the sulfates, are used for this purpose. The pH value of the solutions may be kept constant using suitable buffers, for example sodium phosphate or citric acid. In addition, preservation, for example with formaldehyde solution, p-hydroxybenzoate, sorbic acid or other known preservatives, is advisable for stabilization against bacterial infestation.

Commercial Applications

The new branched substantially unsaturated fatty alcohol sulfates are distinguished by particular stability to oxidation and are therefore suitable for the production of surface-active compositions, preferably laundry detergents, dishwashing detergents, cleaners and softeners, and cosmetic and/or pharmacautical preparations in which they may be present in quantities of 1 to 50% by weight, preferably 5 to 35% by weight and more preferably 10 to 25% by weight.

Laundry Detergents, Dishwashing Detergents, Cleaners and Softeners

Where the branched, substantially unsaturated fatty alcohol sulfates according to the invention are used as raw materials for the production of laundry detergents, dishwashing detergents, cleaners or softeners, they are normally present in liquid form, i.e. as aqueous solutions or pastes; for the production of detergent powders, the water-containing mixtures may be subsequently dried. Liquid preparations may have a non-aqueous component of 5 to 50% by weight and preferably 15 to 35% by weight. In the most simple case, they are aqueous solutions of the mixtures mentioned. However, the liquid detergents may also be substantially water-free compositions. "Substantially water-free" in the context of the present invention means that the composition preferably contains no free water which is not bound as water of crystallization or in a comparable form. In some cases, small quantities of free water are tolerable, more particularly quantities of up to 5% by weight The compositions used in the detergent field may contain other typical ingredients such as, for example, builders, bleaching agents, bleach activators, solvents, detergency boosters, enzymes, enzyme stabilizers, viscosity regulators, redeposition inhibitors, optical brighteners, soil repellents, foam inhibitors, inorganic salts and fragrances and dyes.

Suitable liquid builders are ethylenediamine tetraacetic acid, nitrilotriacetic acid, citric acid and inorganic phosphonic acids such as, for example, the neutrally reacting sodium salts of 1-hydroxyethane-1,1-diphosphonate which may be present in quantities of 0.5 to 5% by weight and preferably 1 to 2% by weight.

A suitable solid builder is, in particular, finely crystalline zeolite containing synthetic and bound water, such as detergent-quality zeolite NaA. However, zeolite NaX and mixtures of NaA and NaX are also suitable. The zeolite may be used in the form of a spray-dried powder or even as an undried stabilized suspension still moist from its production. Where the zeolite is used in the form of a suspension, the suspension may contain small additions of nonionic surfactants as stabilizers, for example 1 to 3% by weight—based on zeolite—of ethoxylated $C_{12-18}$ fatty alcohols containing 2 to 5 ethylene oxide groups or ethoxylated isotridecanols. Suitable zeolites have a mean particle size of less than 10 $\mu$m (volume distribution, as measured by the Coulter Counter Method) and contain preferably 18 to 22% by weight and more preferably 20 to 22% by weight of bound water. Suitable substitutes or partial substitutes for zeolites are crystalline layer-form sodium silicates with the general formula $NaMSi_xO_{2x+1} \cdot yH_2O$, where M is sodium or hydrogen, x is a number of 1.9 to 4 and y is a number of 0 to 20, preferred values for x being 2, 3 or 4. Crystalline layer silicates such as these are described, for example, in European patent application EP 0 164 514 A. Preferred crystalline layer silicates are those in which M in the general formula stands for sodium and x assumes the value 2 or 3. Both β- and γ-sodium disilicates $Na_2Si_2O_5 \cdot yH_2O$ are particularly preferred, β-sodium disilicate being obtainable for example by the process described in International patent application WO 91/08171. Powder-form detergents based on the branched, substantially unsaturated fatty alcohol sulfates according to the invention preferably contain 10 to 60% by weight of zeolite and/or crystalline layer silicates as solid builders, mixtures of zeolite and crystalline layer silicates in any ratio being particularly advantageous. In one particularly preferred embodiment, the detergents contain 20 to 50% by weight of zeolite and/or crystalline layer silicates. Particularly preferred detergents contain up to 40% by weight of zeolite and, more particularly, up to 35% by weight of zeolite, based on water-free active substance. Other suitable ingredients of the detergents are water-soluble amorphous silicates which are preferably used in combination with zeolite and/or crystalline layer silicates. Particularly preferred detergents are those which contain above all sodium silicate with a molar ratio of $Na_2O$ to $SiO_2$ (modulus) of 1:1 to 1:4.5 and preferably 1:2 to 1:3.5. The amorphous sodium silicate content of the detergents is preferably up to 15% by weight and more preferably from 2 to 8% by weight. Phosphates, such as tripolyphosphates, pyrophosphates and orthophosphates, may also be present in the detergents in small quantities. The phosphate content of the detergents is preferably up to 15% by weight and, more particularly, from 0 to 10% by weight. In addition, the detergents may contain layer silicates of natural and synthetic origin. Corresponding layer silicates are known, for example, from patent applications DE 23 34 899 B, EP 0 026 529 A and DE 35 26 405 A. Their suitability for use is not confined to a particular composition or structural formula. However, smectites are preferred, bentonites being particularly preferred. Suitable layer silicates which belong to the group of water-swellable smectites are, for example, those corresponding to the following general formulae:

| | |
|---|---|
| $(OH)_4Si_{8-y}Al_y(Mg_xAl_{4-x})O_{20}$ | montmorillonite |
| $(OH)_4Si_{8-y}Al_y(Mg_{6-z}Li_z)O_{20}$ | hectorite |
| $(OH)_4Si_{8-y}Al_y(Mg_{6-z}Al_z)O_{20}$ | saponite | where x=0 to 4, y=0 to 2 and z=0 to 6. In addition, small quantities of iron may be incorporated in the crystal lattice of the layer silicates corresponding to the above formulae. By virtue of their ion-exchanging properties, the layer silicates may also contain hydrogen, alkali metal and alkaline earth metal ions, more particularly $Na^+$ and $Ca^{2+}$. The quantity of water of hydration is generally in the range from 8 to 20% by weight and is dependent upon the degree of swelling and upon the processing method. Suitable layer silicates are known, for example, from U.S. Pat. No. 3,966, 629, U.S. Pat. No. 4,062, 647, EP 0 026 529 A and EP 0 028 432 A. Layer silicates which have been substantially freed from calcium ions and strongly coloring iron ions by an alkali treatment are preferably used. Useful organic builders are, for example, the polycarboxylic adds preferably used in the form of their sodium salts, such as citric acid, adipic acidic acid, succinic acid, glutaric acid, tartaric acid, sugar acids, aminocarboxylic acids, nitrilotriacetic acid (NTA), providing their use is not ecologically unsafe, and mixtures thereof. Preferred salts are the salts of polycarboxylic acids, such as citric acid, adipic acid, succinic acid, glutaric acid, tartaric acid, sugar acids and mixtures thereof. Suitable polymeric polycarboxylates are, for example, the sodium salts of polyacrylic acid or polymethacrylic add, for example those with a relative molecular weight of 800 to 150,000 (based on add). Suitable copolymeric polycarboxylates are, in particular, those of acrylic acid with methacrylic acid and acrylic acid or methacrylic acid with maleic acid. Copolymers of acrylic acid with maleic acid which contain 50 to 90% by weight of acrylic acid and 50 to 10% by weight of maleic acid are particularly suitable. Their relative molecular weight, based on free acids, is generally in the range from 5,000 to 200,000, preferably in the range from 10,000 to 120,000 and more preferably in the range from 50,000 to 100,000. It is not absolutely essential to use polymeric polycarboxylates. However, if polymeric polycarboxylates are used, detergents containing biodegradable polymers, for example terpolymers which contain acrylic acid and maleic acid or salts thereof and vinyl alcohol or vinyl alcohol derivatives as monomers or acrylic acid and 2-alkyl allyl sulfonic acid or salts thereof and sugar derivatives as monomers are preferred. The terpolymers obtained in accordance with the teaching of German patent applications DE 42 21 381 A and DE 43 00 772 A are particularly preferred. Other suitable builders are polyacetals which may be obtained by reacting dialdehydes with polyol carboxylic acids containing 5 to 7 carbon atoms and at least 3 hydroxyl groups, for example as described in European patent application EP 0 280 223 A. Preferred polyacetals are obtained from dialdehydes, such as glyoxal, glutaraldehyde, terephthalaldehyde and mixtures thereof and from polyol carboxylic acids, such as gluconic acid and/or glucoheptonic acid.

Among the compounds yielding hydrogen peroxide in water which are used as bleaching agents, sodium perborate tetrahydrate and sodium perborate monohydrate are particularly important. Other suitable bleaching agents are, for example, peroxycarbonate, citrate perhydrates and salts of peracids, such as perbenzoates, peroxyphthalates or diperoxydodecanedioic acid. They are normally used in quantities of 8 to 25% by weight Sodium perborate monohydrate is preferred and is used in quantities of 10 to 20% by weight and preferably in quantities of 10 to 15% by weight. By virtue of its ability to bind free water to form the tetrahydrate, it contributes towards increasing the stability of the detergent.

In order to obtain an improved bleaching effect where washing is carried out at temperatures of 60° C. or lower, bleach activators may be incorporated in the preparations. Examples of bleach activators are N-acyl and O-acyl compounds which form organic peracids with hydrogen peroxide, preferably N,N'-tetraacylated diamines, also carboxylic anhydrides and esters of polyols, such as glucose pentaacetate. The bleach activator content of bleach-containing detergents is in the usual range, i.e. preferably between 1 and 10% by weight and more preferably between 3 and 8% by weight. Particularly preferred bleach activators are N,N,N',N'-tetraacetyl ethylenediamine and 1,5-diacetyl-2,4-dioxohexahydro-1,3,5-triazine.

Suitable organic solvents are, for example, monohydric and/or polyhydric alcohols containing 1 to 6 carbon atoms and preferably 1 to 4 carbon atoms. Preferred alcohols are ethanol, propane-1,2-diol, glycerol and mixtures thereof. The detergents preferably contain 2 to 20% by weight and more preferably 5 to 15% by weight of ethanol or a mixture of ethanol and propane-1,2-diol or, more particularly, of ethanol and glycerol. In another possible embodiment, the preparations contain polyethylene glycol with a relative molecular weight of 200 to 2,000 and preferably up to 600 In quantities of 2 to 17% by weight either in addition to the monohydric and/or polyhydric alcohols containing 1 to 6 carbon atoms or on its own. suitable hydrotropes are, for example, toluene sulfonate, xylene sulfonate, cumene sulfonate or mixtures thereof.

Suitable enzymes are those from the dass of proteases, lipases, amylases, cellulases and mixtures thereof. Enzymes obtained from bacterial strains or fungi, such as *Bacillus subtlis, Bacillus licheniformis* and *Streptomyces griseus*, are particularly suitable. Proteases of the subtilisin type are preferably used, proteases obtained from *Bacillus lentus* being particularly preferred. They may be used in quantities of about 0.2 to about 2% by weight. The enzymes may be adsorbed onto supports and/or embedded in membrane materials to protect them against premature decomposition. In addition to the monohydric and polyhydric alcohols and the phosphonates, the detergents may contain other enzyme stabilizers. For example, 0.5 to 1% by weight of sodium formate may be used. It is also possible to use proteases which are stabilized with soluble calcium salts and which have a calcium content of preferably about 1.2% by weight, based on the enzyme. However, it is of particular advantage to use boron compounds, for example boric acid, boron oxide, borax and other alkali metal borates, such as the salts of orthoboric acid ($H_3BO_3$), metaboric acid ($HBO_2$) and pyroboric acid (tetraboric acid $H_2B_4O_7$).

Suitable viscosity regulators are, for example, hydrogenated castor oil, salts of long-chain fatty acids, which are preferably used in quantities of 0 to 5% by weight and more preferably in quantities of 0.5 to 2% by weight, for example sodium, potassium, aluminium, magnesium and titanium stearates or the sodium and/or potassium salts of behenic acid, and other polymeric compounds. Preferred other polymeric compounds include polyvinyl pyrrolidone, urethanes and the salts of polymeric polycarboxylates, for example homopolymeric or copolymeric polyacrylates, polymethacrylates and, in particular, copolymers of acrylic acid with maleic acid, preferably those of 50% to 10% maleic acid. The relative molecular weight of the homopolymers is generally between 1,000 and 100,000 while the relative molecular weight of the copolymers is between 2,000 and 200,000 and preferably between 50,000 and 120,000, based on the free acid. Water-soluble polyacrylates which are crosslinked, for example, with about 1% of a polyallyl ether of sucrose and which have a relative molecular weight above 1,000,000 are also particularly suitable. Examples include the polymers with a thickening effect obtainable under the name of Carbopol® 940 and 941. The crosslinked polyacrylates are preferably used in quantities of not more than 1% by weight and more preferably in quantities of 0.2 to 0.7% by weight The detergents may additionally contain about 5 to 20% by weight of a partly esterified copolymer of the type described in European patent application EP 0 367 049 A. These partly esterified polymers are obtained by copolymerization of (a) at least one $C_{4-28}$ olefin or mixtures of at least one $C_{4-28}$ olefin with up to 20 mole-% of $C_{4-28}$ alkyl vinyl ethers and (b) ethylenically unsaturated dicarboxylic anhydrides containing 4 to 8 carbon atoms in a molar ratio of 1:1 to form copolymers with K values of 6 to 100 and subsequent partial esterification of the copolymers with reaction products, such as $C_{1-13}$ alcohols, $C_{8-22}$ fatty acids, $C_{1-12}$ alkyl phenols, secondary $C_{2-30}$ amines or mixtures thereof, with at least one $C_{2-4}$ alkylene oxide or tetrahydrofuran and hydrolysis of the anhydride groups of the copolymers to carboxyl groups, the partial esterification of the copolymers being continued to such an extent that 5 to 50% of the carboxyl groups of the copolymers are esterified. Preferred copolymers contain maleic anhydride as the ethylenically unsaturated dicarboxylic anhydride. The partly esterified copolymers may be present either in the form of the free acid or preferably in partly or completely neutralized form. The copolymers are advantageously used in the form of an aqueous solution, more particularly in the form of a 40 to 50% by weight solution. The copolymers not only contribute towards the single wash cycle and multiple wash cycle performance of the liquid detergent, they also promote a desirable reduction in viscosity of the concentrated liquid detergents. By using these partly esterified copolymers, it is possible to obtain concentrated aqueous liquid detergents which flow under the sole effect of gravity, i.e. without any need for other shear forces. In a preferred embodiment, the concentrated aqueous liquid detergents contain partly esterified copolymers in quantities of 5 to 15% by weight and, more particularly, in quantities of 8 to 12% by weight.

The function of redeposition inhibitors is to keep the soil detached from the fibers suspended in the wash liquor and thus to prevent discoloration. Suitable redeposition inhibitors are water-soluble, generally organic colloids, for example the water-soluble salts of polymeric carboxylic acids, glue, gelatin, salts of ether carboxylic acids or ether sulfonic acids of starch or cellulose or salts of acidic sulfuric acid esters of cellulose or starch. Water-soluble polyamides containing acidic groups are also suitable for this purpose. Soluble starch preparations and other starch products than those mentioned above, for example degraded starch, aldehyde starches, etc., may also be used. Polyvinyl pyrrolidone is also suitable. However, cellulose ethers, such as carboxymethyl cellulose, methyl cellulose, hydroxyalkyl cellulose, and mixed ethers, such as methyl hydroxyethyl cellulose, methyl hydroxypropyl cellulose, methyl carboxymethyl cellulose and mixtures thereof, and polyvinyl pyrrolidone are preferably used, for example in quantifies of 0.1 to 5% by weight, based on the detergent.

The detergents may contain derivatives of diaminostilbene disulfonic acid or alkali metal salts thereof as optical brighteners. Suitable optical brighteners are, for example, salts of 4,4'-bis-(2-anilino-4-morpholino-1,3,5-triazinyl-6-amino)-stilbene-2,2'-disulfonic acid or compounds of similar structure which, instead of the morpholino group, contain a diethanolamino group, a methylamino group, an anilino group or a 2-methoxyethylamino group. Brighteners of the substituted diphenyl styryl type, for example alkali metal salts of 4,4'-bis-(2-sulfostyryl)-diphenyl, 4,4'-bis-(4-chloro-3-sulfostyryl)-diphenyl or 4-(4-chlorostyryl)-4'-(2-sulfostyryl)-diphenyl, may also be present. Mixtures of the brighteners mentioned above may also be used. Uniformly white granules are obtained if, in addition to the usual brighteners in the usual quantities, for example between 0.1 and 0.5% by weight and preferably between 0.1 and 0.3% by weight, the detergents also contain small quantities, for example $10^{-6}$ to $10^{-3}$% by weight and preferably around $10^{-5}$% by weight, of a blue dye. A particularly preferred dye is Tinolux® (a product of Ciba-Geigy).

Suitable soil repellents are substances which preferably contain ethylene terephthalate and/or polyethylene glycol terephthalate groups, the molar ratio of ethylene terephthalate to polyethylene glycol terephthalate being in the range from 50:50 to 90:10. The molecular weight of the linking polyethylene glycol units is more particularly in the range from 750 to 5,000, i.e. the degree of ethoxylabon of the polymers containing polyethylene glycol groups may be about 15 to 100. The polymers are distinguished by an average molecular weight of about 5,000 to 200,000 and may have a block structure, but preferably have a random structure. Preferred polymers are those with molar ethylene terephthalate: polyethylene glycol terephthalate ratios of about 65:35 to about 90:10 and preferably in the range from about 70:30 to 80:20. Other preferred polymers are those which contain linking polyethylene glycol units with a molecular weight of 750 to 5,000 and preferably in the range from 1,000 to about 3,000 and which have a molecular weight of the polymer of about 10,000 to about 50,000. Examples of commercially available polymers are the products Milease® T (ICI) or Repelotex® SRP 3 (Rhône-Poulenc).

Where the detergents are used in washing machines, it can be of advantage to add conventional foam inhibitors to them. Suitable foam inhibitors are, for example, soaps of natural or synthetic origin which have a high percentage of $C_{18-24}$ fatty acids. Suitable non-surface-active foam inhibitors are, for example, organopolysiloxanes and mixtures thereof with microfine, optionally silanized silica and paraffins, waxes, microcrystalline waxes and mixtures thereof with silanized silica or bi-stearyl ethylenediamide. Mixtures of various foam inhibitors, for example mixtures of silicones, paraffins or waxes, may also be used with advantage. The foam inhibitors, more particularly silicone or paraffin-containing foam inhibitors, are preferably fixed to a granular water-soluble or water-dispersible carrier/support. Mixtures of paraffins and bis-stearyl ethylenediamides are particularly preferred.

The pH value of liquid detergents, more especially concentrated liquid detergents, is generally in the range from 7 to 10.5, preferably in the range from 7 to 9.5 and more preferably in the range from 7 to 8.5. Higher pH values, for example above 9, can be adjusted by using small quantities of sodium hydroxide or alkaline salts, such as sodium carbonate or sodium silicate. The liquid preparations generally have viscosities of 150 to 10,000 mPas (Brookfield viscosimeter, spindle 1,20 r.p.m., 20° C.). The substantially water-free detergents preferably have viscosities of 150 to 5,000 mPas. The viscosity of aqueous detergents is preferably below 2,000 mPas and, more particularly, in the range from 150 to 1,000 mPas.

Production of Solid Compositions

The bulk density of the solid compositions is generally in the range from 300 to 1,200 g/l and more particularly in the range from 500 to 1,100 g/l. They may be produced by any of the known methods, such as mixing, spray drying, granulation and extrusion. Processes in which several components, for example spray-dried components and granulated and/or extruded components, are mixed with one another are particularly suitable. The spray dried or granulated components may also be subsequently treated, for example with nonionic surfactants, more particularly ethoxylated fatty alcohols, by any of the usual methods. In granulation and extrusion processes in particular, any anionic surfactants present are preferably used in the form of a spray dried, granulated or extruded compound either as an added component in the process or as an additive to other granules. The preferred relatively heavy granules with bulk densities above 600 g/l in particular preferably contain components which improve the dispensing behavior and/or the dissolving behavior of the granules. Alkoxylated fatty alcohols containing 12 to 80 moles of ethylene oxide per mole of alcohol, for example tallow fatty alcohol containing 14 EO, 30 EO or 40 EO, and polyethylene glycols with a relative molecular weight of 200 to 12,000 and preferably in the range from 200 to 600, are advantageously used for this purpose.

It is also possible and, depending on the formulation, can be of advantage subsequently to add other individual ingredients of the detergent, for example citrate or citric acid or other polycarboxylates or polycarboxylic acids, polymeric polycarboxylates, zeolite and/or layer silicates, which may optionally be crystalline, to spray-dried, granulated and/or extruded components optionally treated with nonionic surfactants and/or other ingredients which are liquid to wax-like at the processing temperature. A preferred process in this regard is one in which the surface of ingredients of the detergent or the detergent as a whole is subsequently treated to reduce the tackiness of the granules rich in nonionic surfactants and/or to improve their solubility. Suitable surface modifiers are known from the prior art. Besides other suitable surface modifiers, fine-particle zeolites, silicas, amorphous silicates, fatty acids or fatty acid salts, for example calcium stearate, but especially mixtures of zeolite and silicas or zeolite and calcium stearate, are particularly preferred.

Cosmetic and/or Pharmaceutical Preparations

The branched, substantially unsaturated fatty alcohol sulfates according to the invention may be used for the production of cosmetic and/or pharmaceutical preparations, for example hair shampoos, hair lotions, foam baths, shower baths, creams, gels, lotions, alcoholic and aqueous/alcoholic solutions, emulsions, wax/fat compounds, stick preparations, powders or ointments. These preparations may also contain mild surfactants, oil components, emulsifiers. superfatting agents, pearlizing waxes, consistency factors, thickeners, polymers, silicone compounds, fats, waxes, stabilizers, biogenic agents, deodorants, antiperspirants, antidandruff agents, film formers, swelling agents, UV protection factors, antioxidants, hydrotropes, preservatives, insect repellents, self-tanning agents, solubilizers, perfume oils, dyes and the like as further auxiliaries and additives.

Typical examples of suitable mild, i.e. particularly dermatologically compatible, surfactants are fatty alcohol polglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines and/or protein fatty acid condensates, preferably based on wheat proteins.

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic adds with linear $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl paimitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of hydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/tri-glyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons, for example squalane, squalene or dialkyl cyclohexanes.

Suitable emulsifiers are, for example, nonionic surfactants from at least one of the following groups:

- products of the addition of 2 to 30 moles of ethylene oxide and/or 0 to 5 moles of propylene oxide onto linear $C_{8-22}$ fatty alcohols, $C_{12-22}$ fatty acids and alkyl phenols containing 8 to 15 carbon atoms in the alkyl group and alkylamines containing 8 to 22 carbon atoms in the alkyl group;
- alkyl and/or alkenyl oligoglycosides containing 8 to 22 carbon atoms in the alkyl group and ethoxylated analogs thereof;
- products of the addition of 1 to 15 moles of ethylene oxide with castor oil and/or hydrogenated castor oil;
- products of the addition of 15 to 60 moles of ethylene oxide with castor oil and/or hydrogenated castor oil;
- partial esters of glycerol and/or sorbitan with unsaturated, linear or saturated, branched fatty acids containing 12 to 22 carbon atoms and/or hydroxycarboxylic acids containing 3 to 18 carbon atoms and addition products thereof with 1 to 30 moles of ethylene oxide;
- partial esters of polyglycerol (average degree of self-condensation 2 to 8), polyethylene glycol (molecular weight 400 to 5,000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and addition products thereof with 1 to 30 moles of ethylene oxide;
- mixed esters of pentaerythritol, fatty acids, citric acid and fatty alcohol according to DE 11 65 574 PS and/or mixed esters of fatty acids containing 6 to 22 carbon atoms, methyl glucose and polyols, preferably glycerol or polyglycerol,
- mono-, di- and trialkyl phosphates and mono, di- and/or tri-PEG-alkyl phosphates and salts thereof,
- wool wax alcohols,
- polysiloxane/polyalkyl/polyether copolymers and corresponding derivatives,
- polyalkylene glycols and
- glycerol carbonate.

The addition products of ethylene oxide and/or propylene oxide with fatty alcohols, fatty acids, alkylphenols or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide with glycerol are known as refatting agents for cosmetic formulations from DE 20 24 051 PS.

Alkyl and/or alkenyl oligoglycosides, their production and their use are known from the prior art. They are produced in particular by reacting glucose or oligosaccharides with primary alcohols containing 8 to 18 carbon atoms. So far as the glucoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride. ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 moles of ethylene oxide with the partial glycerides mentioned are also suitable.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricnoleate, sorbitan sesquiricinoleate, sorbitan diricinoleate, sorbitan tiridcnoleate, sorbitan monohydroxystearate, sorbitan sesquihydroxystearate, sorbitan dihydroxystearate, sorbitan trihydroxystearate, sorbitan rmonotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 moles of ethylene oxide with the sorbitan esters mentioned are also suitable.

Typical examples of suitable polyglycerol esters are Polyglyceryl-2 Dipolyhydroxystearate (Dehymuls® PGPH), Polyglyceridn-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate isostearate and mixtures thereof.

Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 moles of ethylene oxide.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactents are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glydnes, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminoproplonate and $C_{12/18}$ acyl sarcosine.

Finally, other suitable emulsifiers are cationic surfactants, those of the esterquat type, preferably methyl-quatemized difatty acid triethanolamine ester salts, being particularly preferred.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether, fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Suitable thickeners are, for example, Aerosil types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable catlonic polymers are, for example, cationic cellulose derivatives such as, for example, the quatemized hydroxyethyl cellulose obtainable from Amerchol under the name of Polymer JR 400®, cationic starch, copolymers of diallyl ammonium salts and acrylamides, quatemized vinyl pyrrolidone/vinyl imidazole polymers such as, for example, Luviquat® (BASF), condensation products of polyglycols and amines, quatemized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2 252 840 A and crosslinked water-soluble polymers thereof, cationic chitin derivatives such as, for example, quatemized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C-17, Jaguar® C-16 of Celanese, quatemized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobomyl acrylate copolymers, methyl vinyleather/maleic anhydride copolymers and esters thereof, uncrosslinked and polyol-crosslinked polyacrylic acids, acrylamidopropyl trimethylammonium chloride/acrylate copolymers, octylacrylamide/methyl methacrylateltert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resinlIke at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 9A, 27 (1976).

Typical examples of fats are glycerides while suitable waxes are inter alia natural waxes such as, for example, candelilla wax, camauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes, micro-waxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricnoleate may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers.

Basically, suitable germ inhibitors are any substances which act against gram-positive bacteria such as, for example, 4-hydroxybenzoic acidand salts and esters thereof, N-(4-chlorophenyl)-N'-(3,4-dichlorophenylyurea, 2,4,4'-trichloro-2'-hydroxydiphenylether (triclosan), 4-chloro-3,5-dimethylphenol, 2,2'-methylene-bis-(6-bromo chlorophenol), 3-methyl-4-(1-methylethyl)-phenol, 2-benzyl-4-chlorophenol, 3-(4-chloro-phenoxy)-propane-1,2-diol, 3-iodo-2-propinyl butyl carbamate, chlor-hexidine, 3,4,4'-trichlorocarbanilide (TTC), antibacterial perfumes, thymol, thyme oil, eugenol, nettle oil, menthol, mint oil, farnesol, phenoxyethanol, glycerol monolaurate (GML), diglycerol monocaprate (DMC), salicylic acid-N-alkylamides such as, for example, salicylic acid-n-octyl amide or salicylic acid-n-decyl amide.

Suitable enzyme inhibitors are, for example, esterase inhibitors. Esterase inhibitors are preferably trialkyl citrates, such as trimethyl cirate, tripropyl citrate, triisopropyl citrate, tributyl citrate and, in particular, triethyl citrate (Hydagen® CAT, Henkel KGaA, Düsseldorf, FRG). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of ladanum or styrax or certain abietic acid derivatives as their principal component Odor maskers are perfumes or perfume oils which, besides their odor-masking function, impart their particular perfume note to the deodorants. Suitable perfume oils are, for example, mixtures of natural and synthetic perfumes. Natural perfumes include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cydohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cycdamen aldehyde, hydroxy-citronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evemyl, iraldein gamma, phenylacetic acid, geranyl acetate, benzyl acetate, rose oxide, romillat, irotyl and floramat.

Antiperspirants reduce perspiration and thus counteract underarm wetness and body odor by influencing the activity of the eccrine sweat glands. Aqueous or water-free antiperspirant formulations typically contain the following ingredients:

astringent active principles, oil components, nonionic emulsifiers, co-emulsifiers, consistency factors, auxiliaries in the form of, for example, thickeners or complexing agents and/or nonaqueous solvents such as, for example, ethanol, propylene glycol and/or glycerol.

Suitable astringent active principles of antiperspirants are, above all, salts of aluminium, zirconium or zinc. Suitable anthydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlomhydrate, aluminium zirconium pentachlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example, inflammation-inhibiting, skin-protecting or pleasant-smelling essential oils, synthetic skin-protecting agents and/or oil-soluble perfume oils.

Typical water-soluble additives are, for example, preservatives, water-soluble perfumes, pH adjusters, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Suitable antidandruff agents are climbazol, octopirox and zinc pyrithione.

Standard film formers are, for example, chitosan, microcrystalline chitosan, quatemized chitosan, polyvinyl pyrrolidone, vinyl pyrrolidone/vinyl acetate copolymers, polymers of the acrylic acid series, quatemary cellulose derivatives, collagen, hyaluronic acid and salts thereof and similar compounds.

Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108. 95 (1993).

Examples of UV protection factors include organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

- 3-benzylidene camphor or 3-benzylidene norcamphor and derivatives thereof, for example 3-(4-methylbenzylidene)-camphor, as described in EP 0693471 B1;
- 4-aminobenzoic acid derivatives, preferably 4-(dimethylamino)-benzoic acid-2-ethyihexyl ester, 4-(dimethylamino)benzoic acid-2-octyl ester and 4-(dimethylamino)-benzoic acid amyl ester,
- esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenyicinnamic acid-2-ethylhexyl ester (Octocrylene);
- esters of salicylic acid, preferably salicylic acid-2-ethylhexyl ester, salicylic acid-4-isopropylbenzyl ester, salicylic acid homomenthyl ester,
- derivatives of benzophenone, preferably 2-hydroxy-4-methoxybenzophenone, 2-hydroxy-4-methoxy-4'-methylbenzophenone, 2,2'-dihydroxy-4-methoxybenzophenone;
- esters of benzalmalonic acid, preferably 4-methoxybenzalmalonic acid di-2-ethylhexyl ester;
- triazine derivatives such as, for example, 2,4,6-trianilino-(p-carbo-2'-ethyl-1'-hexyloxy)-1,3,5-triazine and Octyl Triazone, as described in EP 0 818 450 A1, or Dioctyl Butamido Triazine (Uvasorb® HEB);
- propane-1,3-diones such as, for example, 1-(4-tert.butylphenyl)-3-(4'-methoxyphenyl)-propane-1,3-dione;
- ketotricyclo(5.2.1.0)decane derivatives, as described in EP 0 694 521 B1.

Suitable water-soluble substances are

- 2-phenylbenzimidazole-5-sulfonic acid and alkali metal, alkaline earth metal, ammonium, alkylammonium, alkanolammonium and glucammonium salts thereof;
- sulfonic acid derivatives of benzophenones, preferably 2-hydroxy-4-methoxybenzophenone-5-sulfonic acid and salts thereof;
- sulfonic acid derivatives of 3-benzylidene camphor such as, for example, 4-(2-oxo-3-bomylidenemethyl)-benzene sulfonic acid and 2-methyl-5-(2-axo-3-bomylidene)-sulfonic acid and salts thereof.

Typical UV-A filters are, in particular, derivatives of benzoyl methane such as, for example 1-(4'-tert.butylphenyl3-(4'-methoxyphenyl)-propane-1,3-dione, 4-tert-butyl-4'-methoxydibenzoylmethane (Parsol 1789), 1-phenyl-3-(4'-isopropylphenyl)propane-1,3-dione and the eneamine compounds described in DE 19712033 A1 (BASF). The UV-A and UV-B filters may of course also be used in the form of mixtures. Besides the soluble substances mentioned, insoluble pigments, i.e. finely dispersed metal oxides or salts, may also be used for this purpose. Examples of suitable metal oxides are, in particular, zinc oxide and titanium dioxide and also oxides of iron, zirconium, silicon, manganese, aluminium and cerium and mixtures thereof. Silicates (talcum), barium sulfate and zinc stearate may be used as salts. The oxides and salts are used in the form of the pigments for skin-care and skin-protecting emulsions. The particles should have an average diameter of less than 100 nm, preferably from 5 to 50 nm and more preferably from 15 to 30 nm. They may be spherical in shape although ellipsoidal particles or other non-spherical particles may also be used. The pigments may also be surface-treated, i.e. hydrophilicized or hydrophobicized. Typical examples are coated titanium dioxides such as, for example, Titandioxid T 805 (Degussa) or Eusolex® T2000 (Merck). Suitable hydrophobic coating materials are, above all, silicones and particularly trialkoxyoctyl silanes or simethicones. So-called micro- or nanopigments are preferably used in sun protection products. Micronized zinc oxide is preferably used. Other suitable UV filters can be found in P. Finkel's review in SÖFW-Journal 122, 543 (1996).

Besides the two above-mentioned groups of primary protection factors, secondary protection factors of the anti-oxidant type may also be used. Secondary sun protection factors of the antioxidant type interrupt the photochemical reaction chain which is initiated when UV rays penetrate into the skin. Typical examples of suitable antioxidants are amino acids (for example glycine, histidine, tyrosine, tryptophane) and derivatives thereof, Imidazoles (for example urocanic acid) and derivatives thereof, peptides, such as D,L-camosine, D-camosine, L-camosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their safts, dilauryfthiodipropionate, distearylthiodipropionate, thiodipropionic acid and derivatives thereof (esters, ethers, peptides, lipids, nucleotides, nucleosides and salts) and sulfoxlmine compounds (for example butlonine sulfoximines, homocysteine sulfoximine, butionine sulfones, penta-, hexa- and hepta-thionine sulfoximine) In very small compatible dosages (for example pmole to pmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty adds and derivatives thereof (for example γ-linolenic acid, linoleic acid, oleic acdd), folic acid and derivatives thereof, ubiquinone and ubiquinol and derivatives thereof, vitamin C and derivatives thereof (for example ascorbyl palmitate, Mg ascorbyl phosphate, ascorbyl acetate), locopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, camosine, butyl hydroxytoluene, butyl hydroxyanisole, nordihydroguaiac resin acid, nordihydroguaiaretic acid, trihydroxy-butyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (safts, esters, ethers, sugars, nuccleotides, nucleosides, peptides and lipids).

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Ethyl Butylacetyl-aminopropionate. A suitable self-tanning agent is dihydroxyacetone.

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl proplonate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the Ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cycdamen aidehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evemyl, iraldein gamma, phenylacetic acid, geranyl acetate, benzyl acetate, rose oxide, romillat, irotyl and floramat.

Suitable dyes are any of the substances suitable and approved for cosmetic purposes as listed, for example, in the publication "Kosmetische Färbemittel" of the Farbstoffkommission der Doutschen Forschungs-gemeinschaft, Verlag Chemie, Weinhelm, 1984, pages 81 to 106. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular composition. The compositions may be produced by standard hot or cold processes and are preferably produced by the phase inversion temperature method.

EXAMPLES

Example 1

23 kg of the monomer fatty acid Edenor® 935 (Henkel KGaA) were esterified with 20 kg of methanol for 2 h at 240° C./100 bar. After removal of the water/methanol mixture, the same quantity of fresh methanol was added and the procedure was repeated twice. The ester thus obtained had an acid value of 0.8. The methyl ester was hydrogenated on a fixed-bed Zn/Cr catalyst with the double bond intact The throughput of methyl ester was 0.5 unit by volume per hour, based on the total volume of the reactor. After removal of the methanol, the crude alcohol was distilled (3% first runnings, 90% main runnings, 6% residue). The resulting alcohol had a hydroxyl value of 192, a saponification value of 0.9 and an iodine value of 74 (solidus point 25.8° C.). 586 g (2 mol) of the isooleyl alcohol obtained were sulfated with sulfur trioxide in a molar ratio of 1:0.95 in a falling film reactor at a temperature of 25° C., the sulfur trioxide being 3% diluted with nitrogen. Immediately after leaving the reactor, the reaction product was neutralized with aqueous sodium hydroxide solution and the neutralized product was post-hydrolyzed for 1 hour at pH 10. Analysis produced the following results:

| | |
|---|---|
| dry residue | 49.0% by weight |
| detersive substance (Epton) | 35.1% by weight |
| unsulfated | 13.0% by weight |
| sodium sulfate | 0.2% by weight |

Example 2

Monomer fatty acid was substantially freed from straight-chain saturated fatty acids by crystallization from methanol/ water (Emersol process). Around 20% by weight of fatty acid, predominantly palmltic and stearic acid, was removed in this way. The liquid fatty acid mixture obtained after removal of the solvent by distillation had a titer of 5° C. and was first converted into the methyl ester and then hydrogenated to the unsaturated fatty alcohol in the same way as in Example 1. The unsaturated fatty alcohol had a hydroxyl value of 191, a saponification value of 1.7 and an iodine value of 87 (solidus point 3.8° C.). 586 g (2 mol) of the isooleyl alcohol thus obtained were sulfated with sulfur trioxide in a molar ratio of 1:1.05 in a falling film reactor at a temperature of 30° C., the sulfur trioxide being 5% diluted with nitrogen. Immediately after leaving the reactor, the reaction product was neutralized with aqueous sodium hydroxide solution and the neutralized product was post-hydrolyzed for 1 hour at pH 10. Analysis produced the following results:

| | |
|---|---|
| dry residue | 49.8% by weight |
| detersive substance (Epton) | 38.2% by weight |
| unsulfated | 11.3% by weight |
| sodium sulfate | 0.4% by weight |

Tables 1 and 2 below shows a number of formulation examples ((1–6) light duty detergent, (7–9) heavy duty detergent, (10) toilet bar soap, (11–15) manual dishwashing detergent, (16,17) machine dishwashing detergent, (18–20) cleaner, (21–24) hair rinse, (25–26) hair conditioner, (27–28) shower bath, (29) shower gel, (30) wash lotion, (31–34) "two-in-one" shower bath, (35–40) shampoo, (41–45) foam bath, (46 soft cream), (47,48) moisturizing emulsion, (49,50) night cream).

TABLE 1

Detergent preparations (water, preservative to 100% by weight)

| Composition | 1 | 2 | 3 | 4 | 5 | 6 | 7 | 8 | 9 | 10 |
|---|---|---|---|---|---|---|---|---|---|---|
| Maranill ® Paste A 55<br>Dodecylbenzenesulfonate, sodium salt | — | 23.6 | — | 19.0 | — | — | 11.0 | 7.0 | — | — |
| Fatty alcohol sulfate of Example 1 | 1.0 | 1.0 | 1.0 | 1.0 | 1.0 | 1.0 | 1.0 | 1.0 | 5.0 | 5.0 |
| Sulfopon ® 1218 W<br>Lauryl stearyl sulfate, sodium salt | 5.5 | — | 14.5 | — | — | — | — | 3.0 | 7.0 | 30.0 |
| Texapon ® N<br>Lauryl alcohol + 2EO sulfate, sodium salt | — | — | — | — | — | 9.6 | — | — | — | — |
| Dehyquart ® AU 56<br>Methyl-quaternized dipalm oil fatty acid triethanolammonium ester, methosulfate | — | — | — | — | 6.7 | — | — | — | — | — |
| Comperlan ® 100<br>Cocofatty acid ethanolamide | — | — | — | — | — | — | — | — | — | 10.0 |
| Dehydol ® O8<br>Octanol + 8EO | — | — | — | — | — | 30.0 | — | — | — | — |
| Dehydol ® LT5<br>Lauryl stearyl alcohol + 5EO | — | — | — | — | — | — | 10.0 | — | 6.0 | — |
| Dehydol ® LT 7<br>Lauryl stearyl alcohol + 7EO | 12.0 | — | — | — | 10.2 | — | — | 2.0 | 4.0 | — |
| Eumulgin ® WO 7<br>Oleyl alcohol + 7 EO | — | — | 10.0 | 4.0 | — | — | — | — | — | — |
| Eumulgin ® RT 40<br>Castor oil + 40EO | — | — | — | — | — | — | — | — | — | 5.0 |
| Glucopan ® 600 CS UP<br>Lauryl glucoside | 4.0 | 5.0 | 11.0 | 15.0 | 6.0 | 19.5 | — | — | 1.0 | — |
| Edenor ® K 1218<br>Cocofatty acid | 6.0 | — | 4.0 | — | — | 12.0 | — | — | — | — |
| Sokalan ® CP5<br>Maleic acid/acrylic acid copolymer, sodium salt | — | — | — | 5.0 | — | — | — | 4.0 | 5.5 | — |
| Sodium carbonate | — | 2.0 | — | 7.0 | — | — | 13.0 | 7.0 | 10.0 | — |
| Sodium sulfate | — | — | — | 19.0 | — | — | — | 10.0 | 9.5 | 45.0 |
| Sodium tripolyphosphate | — | 20.0 | — | — | — | — | — | — | — | — |
| Zeolite A | — | — | — | 25.0 | — | — | 39.0 | 25.0 | 32.5 | — |
| Amylase | — | — | — | — | — | — | 0.2 | — | 0.2 | — |
| Cellulase | — | — | — | — | — | — | 0.2 | — | — | — |
| Lipase | 0.8 | — | — | — | — | — | 0.2 | 0.7 | 0.1 | — |
| Protease | — | — | — | — | — | — | 0.2 | 0.3 | 0.1 | — |
| Glycerol | 3.0 | — | — | — | — | — | — | — | — | — |
| Propylene glycol | 7.0 | — | 5.0 | — | — | — | — | — | — | — |
| Ethanol | 5.0 | — | 5.0 | — | — | 7.0 | — | — | — | — |
| Protil ® N<br>Sodium silicate | — | — | — | 3.0 | — | — | — | — | — | — |
| Dehydran ® 760<br>Silicon/Paraffin on carrier | — | — | — | 7.0 | — | — | 4.0 | 5.0 | 4.5 | — |
| Polyvinyl pyrrolidone | — | — | — | — | — | — | 0.3 | 1.0 | 0.8 | — |
| Sodium hydroxide | 5.5 | — | 5.0 | — | — | 7.6 | — | — | — | — |
| Sodium hydrogen carbonate | — | — | — | — | — | — | 7.0 | 9.0 | 5.5 | — |
| Sodium chloride | 0.1 | — | — | — | 0.1 | — | 4.0 | 12.0 | 4.0 | 5.0 |
| Composition | 11 | 12 | 13 | 14 | 15 | 16 | 17 | 18 | 19 | 20 |
| Maranill ® Paste A 55<br>Dodecylbenzenesulfonate, sodium salt | 20.0 | — | — | — | — | — | — | — | — | 6.0 |

TABLE 1-continued

| Detergent preparations (water, preservative to 100% by weight) | | | | | | | | | | |
|---|---|---|---|---|---|---|---|---|---|---|
| Fatty alcohol sulfate of Example 1 | 1.0 | 1.0 | 1.0 | 1.0 | 1.0 | 1.0 | 1.0 | 1.0 | 1.0 | 1.0 |
| Texapon ® NSO<br>Lauryl alcohol + 2EO sulfate, sodium salt | 3.0 | 15.0 | — | — | 20.0 | — | — | 2.0 | — | — |
| Texapon ® N70<br>Lauryl alcohol + 2EO sulfate, sodium salt | — | — | 9.0 | — | — | — | — | — | — | — |
| Texapon ® LS 35<br>Lauryl alcohol + 3.5EO sulfate, sodium salt | — | 10.0 | 2.0 | 5.0 | — | — | — | — | 2.0 | — |
| Texapon ® 842<br>Octyl sulfate, sodium salt | 5.0 | 3.5 | — | — | — | — | — | — | — | — |
| Alkane sulfonate C13/17 | — | — | — | 12.5 | 18.0 | — | — | — | — | — |
| Glucopon ® 600 CS UP<br>Lauryl glucoside | 3.0 | 2.0 | 15.0 | 4.0 | — | — | — | 1.0 | — | — |
| Dehydol ® O10<br>Octanol + 10EO | — | — | — | — | 8.0 | — | — | — | — | — |
| Dehydol ® 980<br>Lauryl myristyl alcohol + 1PO + 6EO | — | — | — | — | — | — | — | — | 1.0 | 2.0 |
| Dehydol ® LS 54<br>Lauryl alcohol + 5EO + 4PO | — | — | — | — | — | 15.0 | — | — | — | — |
| Dehydol ® LS 104<br>Lauryl alcohol + 10EO butyl ether | — | — | — | — | — | — | 10.0 | — | — | — |
| Dehyton ® K<br>Cocofatty acid amidopropyl betaine | — | 3.5 | 5.0 | — | — | — | — | — | — | — |
| Sokalan ® DCS<br>Succinic acid/glutaric acid/adipic acid mixture | — | — | 2.5 | — | — | — | — | — | — | — |
| Ethanol | — | — | 8.0 | — | — | — | — | — | — | — |
| Isoproyl alcohol | — | — | — | — | — | — | — | — | — | 3.0 |
| Butyl diglycol | — | — | — | — | — | — | — | — | — | 1.5 |
| Cumene sulfonate, sodium salt | — | — | — | — | — | 20.0 | 13.0 | — | — | — |
| Sodium hydroxide | — | — | 1.5 | — | — | — | — | — | — | — |
| Ammonia | — | — | — | — | — | — | — | — | — | 0.5 |
| Hydrogen peroxide | — | — | — | — | — | — | — | 5.0 | 5.0 | — |
| Turpinal ® 4NL<br>Tetrasodium editronate | — | — | — | — | — | — | — | 0.3 | 0.3 | — |
| Citric acid | 0.2 | 0.2 | 0.2 | 0.2 | 0.2 | — | 5.0 | — | — | — |

TABLE 2

| Cosmetic preparations (water, preservative to 100% by weight) | | | | | | | | | | |
|---|---|---|---|---|---|---|---|---|---|---|
| Composition (INCl) | 21 | 22 | 23 | 24 | 25 | 26 | 27 | 28 | 29 | 30 |
| Texapon ® NSO<br>Sodium Laureth Sulfate | — | — | — | — | — | — | 26.0 | 26.0 | 15.0 | — |
| Fatty alcohol sulfate of Example 1 | 1.0 | 1.0 | 1.0 | 1.0 | 1.0 | 1.0 | 12.0 | 12.0 | 10.0 | 1.0 |
| Texapon ® SB 3<br>Disodium Laureth Sulfosuccinate | — | — | — | — | — | — | — | — | 10.0 | — |
| Plantacare ® 818<br>Coco Glucosides | — | — | — | — | — | — | 7.0 | 7.0 | 6.0 | — |
| Plantacare ® PS 10<br>Sodium Laureth Sulfate (and) Coco Glucosides | — | — | — | — | — | — | — | — | — | 12.0 |
| Dehyton ® PK 45<br>Cocamidopropyl Betaine | — | — | — | — | — | — | — | — | 10.0 | — |
| Dehyquart ® A<br>Cetrimonium Chloride | 2.0 | 2.0 | 2.0 | 2.0 | 4.0 | 4.0 | — | — | — | — |
| Dehyquart L ® 80<br>Dococoylmethylethoxymonium Methosulfate (and) Propyleneglycol | 1.2 | 1.2 | 1.2 | 1.2 | 0.6 | 0.6 | — | — | — | — |
| Eumulgin ® B2<br>Ceteareth-20 | 0.8 | 0.8 | — | 0.8 | — | 1.0 | — | — | — | — |
| Eumulgin ® VL 75<br>Lauryl Glucoside (and) Polyglyceryl-2 Polyhydroxystearate (and) Glycerin | — | — | 0.8 | — | 0.8 | — | — | — | — | — |
| Lanette ® O<br>Cetearyl Alcohol | 2.5 | 2.5 | 2.5 | 2.5 | 3.0 | 2.5 | — | — | — | — |
| Cutina ® GMS<br>Glyceryl Stearate | 0.5 | 0.5 | 0.5 | 0.5 | 0.5 | 1.0 | — | — | — | — |
| Cetiol ® HE<br>PEG-7 Glyceryl Cocoate | 1.0 | — | — | — | — | — | — | — | 1.0 | — |
| Cetiol ® PGL<br>Hexyldecanol (and) Hexyldecyl laurate | — | 1.0 | — | — | 1.0 | — | — | — | — | — |
| Eutanol ® G<br>Octyldodecanol | — | — | 1.0 | 1.0 | — | 1.0 | — | — | — | — |
| Nutrilan ® Keratin W | — | — | — | 2.0 | — | — | — | — | — | — |

TABLE 2-continued

Cosmetic preparations (water, preservative to 100% by weight)

| | | | | | | | | | | |
|---|---|---|---|---|---|---|---|---|---|---|
| Hydrolyzed Keratin Lamesoft ® LMG Glyceryl Laurate (and) Potassium Cocoyl Hydrolyzed Collagen | — | — | — | — | — | — | 3.0 | 2.0 | 4.0 | — |
| Euperlan ® PK 3000 AM Glycol Distearate (and) Laureth-4 (and) Cocamidopropyl Betaine | — | — | — | — | — | — | — | 3.0 | 5.0 | 5.0 |
| Generol ® 122 N Soja Sterol | — | — | — | — | 1.0 | 1.0 | — | — | — | — |
| Highcareen ® GS Betaglucan | 1.0 | 1.0 | 1.0 | 1.0 | 1.0 | 1.0 | 1.0 | 1.0 | 1.0 | 1.0 |
| Hydragen ® CMF Chitosan | 1.0 | 1.0 | 1.0 | 1.0 | 1.0 | 1.0 | 1.0 | 1.0 | 1.0 | 1.0 |
| Copherol ® 12250 Tocopherol Acetate | — | — | 0.1 | 0.1 | — | — | — | — | — | — |
| Arylpon ® F Laureth-2 | — | — | — | — | — | — | 3.0 | 3.0 | 1.0 | — |
| Sodium Chloride | — | — | — | — | — | — | — | 1.5 | — | 1.5 |

| Composition (INCI) | 31 | 32 | 33 | 34 | 35 | 36 | 37 | 38 | 39 | 40 |
|---|---|---|---|---|---|---|---|---|---|---|
| Texapon ® NSO Sodium Laureth Sulfate | 15.0 | 15.0 | 10.0 | — | 20.0 | 8.0 | — | — | — | — |
| Texpon ® K 14 S | — | — | — | — | — | — | — | — | 8.0 | 15.0 |
| Fatty alcohol sulfate of Example 1 | 5.0 | 5.0 | 2.4 | 1.0 | 5.0 | 3.0 | 1.0 | 1.0 | 3.0 | 8.0 |
| Texapon ® SB 3 Disodium Laureth Sulfosuccinate | — | — | — | — | — | 7.0 | — | — | — | — |
| Plantacare ® 818 Coco Glucosides | 5.0 | 5.0 | 4.0 | — | — | — | — | — | 6.0 | 4.0 |
| Plantacare ® 2000 Decyl Glucoside | — | — | — | — | 5.0 | 4.0 | — | — | — | — |
| Plantacare ® PS 10 Sodium Laureth Sulfate (and) Coco Glucosides | — | — | — | 40.0 | — | — | 16.0 | 17.0 | — | — |
| Dehyton ® PK 45 Cocamidopropyl Betaine | 20.0 | 20.0 | — | — | 8.0 | — | — | — | — | 7.0 |
| Eumulgin ® B1 Ceteareth-12 | — | — | — | — | 1.0 | — | — | — | — | — |
| Eumulgin ® B2 Ceteareth-20 | — | — | — | 1.0 | — | — | — | — | — | — |
| Lameform ® TGI Polyglyceryl-3 Isostearate | — | — | — | 4.0 | — | — | — | — | — | — |
| Dehymuls ® PGPH Polyglyceryl-2- Dipolyhydroxystearate | — | — | 1.0 | — | — | — | — | — | — | — |
| Monomuls ® 90-L 12 Glyceryl Laurate | — | — | — | — | — | — | — | — | 1.0 | 1.0 |
| Cetiol ® HE PEG-7 Glyceryl Cocoate | — | 0.2 | — | — | — | — | — | — | — | — |
| Eutanol ® G Octyldodecanol | — | — | — | 1.0 | — | — | — | — | — | — |
| Nutrilan ® Keratin W Hydrolyzed Keratin | — | — | — | — | — | — | — | — | 2.0 | 2.0 |
| Nutrilan ® I Hydrolyzed Collagen | 1.0 | — | — | — | — | 2.0 | — | 2.0 | — | — |
| Lamesoft ® LMG Glyceryl Laurate (and) Potassium Cocoyl Hydrolyzed Collagen | — | — | — | — | — | — | — | — | 1.0 | 5.0 |
| Gluadin ® WK Sodium Cocoyl Hydrolyzed Wheat Protein | 1.0 | 1.5 | 4.0 | 1.0 | 3.0 | 1.0 | 2.0 | 2.0 | 2.0 | — |
| Euperlan ® PK 3000 AM Glycol Distearate (and) Laureth-4 (and) Cocamidopropyl Betaine | 5.0 | 3.0 | 4.0 | — | — | — | — | 3.0 | 3.0 | — |
| Panthenol | — | — | 1.0 | — | — | — | — | — | — | — |
| Arylpon ® F Laureth-2 | 2.6 | 1.6 | — | 1.0 | 1.5 | — | — | — | — | — |
| Highcareen ® GS Betaglucan | 1.0 | 1.0 | 1.0 | 1.0 | 1.0 | 1.0 | 1.0 | 1.0 | 1.0 | 1.0 |
| Hydragen ® CMF Chitosan | 1.0 | 1.0 | 1.0 | 1.0 | 1.0 | 1.0 | 1.0 | 1.0 | 1.0 | 1.0 |
| Sodium Chloride | — | — | — | — | — | 1.6 | 2.0 | 2.2 | — | 3.0 |
| Glycerin (86% by weight) | — | 5.0 | — | — | — | — | — | 1.0 | 3.0 | — |

| Composition (INCI) | 41 | 42 | 43 | 44 | 45 | 46 | 47 | 48 | 49 | 50 |
|---|---|---|---|---|---|---|---|---|---|---|
| Texapon ® NSO Sodium Laureth Sulfate | — | 22.0 | 22.0 | — | 20.0 | — | — | — | — | — |
| Fatty alcohol sulfate of Example 2 | 1.0 | 8.0 | 8.0 | 1.0 | 5.0 | 1.0 | 1.0 | 1.0 | 1.0 | 1.0 |
| Plantacare ® 818 | — | 10.0 | — | — | 20.0 | — | — | — | — | — |

TABLE 2-continued

| Cosmetic preparations (water, preservative to 100% by weight) | | | | | | | | | | |
|---|---|---|---|---|---|---|---|---|---|---|
| Coco Glucoaldes<br>Plantacare ® PS 10 | 22.0 | — | 5.0 | 22.0 | — | — | — | — | — | — |
| Sodium Laureth Sulfate (and) Coco Glucosides<br>Dehyton ® PK 45 | 15.0 | 10.0 | 15.0 | 15.0 | 20.0 | — | — | — | — | — |
| Cocamidopropyl Betaine<br>Emulgade ® SE | — | — | — | — | — | 5.0 | 5.0 | 4.0 | — | — |
| Glyceryl Stearate (and) Ceteareth 12/20<br>(and) Cetearyl Alcohol (and) Cetyl Palmitate<br>Lameform ® TGI | — | — | — | — | — | — | — | — | 4.0 | — |
| Polyglyceryl-3 Isostearate<br>Dehymuls ® PGPH | — | — | — | — | — | — | — | — | — | 4.0 |
| Polyglyceryl-2 Dipolyhydroxysteearate<br>Monomuls ® 90-O 18 | — | — | — | — | — | — | — | — | 2.0 | — |
| Glyceryl Oleate<br>Cetiol ® HE | 2.0 | — | — | 2.0 | 5.0 | — | — | — | — | 2.0 |
| PEG-7 Glyceryl Cocoate<br>Cetiol ® OE | — | — | — | — | — | — | — | — | 5.0 | 6.0 |
| Dicaprylyl Ether<br>Cetiol ® PGL | — | — | — | — | — | — | — | 3.0 | 10.0 | 9.0 |
| Hexyldecanol (and) Hexyldecyl Laurate<br>Cetiol ® SN | — | — | — | — | — | 3.0 | 3.0 | — | — | — |
| Cetearyl Isononanoate<br>Cetiol ® V | — | — | — | — | — | 3.0 | 3.0 | — | — | — |
| Decyl Oleate<br>Myritol ® 318 | — | — | — | — | — | — | — | 3.0 | 5.0 | 5.0 |
| Coco Caprylate Caprate<br>Bees Wax | — | — | — | — | — | — | — | — | 7.0 | 5.0 |
| Nutrilan ® Elastin E20<br>Hydrolyzed Elastin | — | — | — | — | — | 2.0 | — | — | — | — |
| Nutrilan ® I-50<br>Hydrolyzed Collagen | — | — | — | — | 2.0 | — | 2.0 | — | — | — |
| Gluadin ® AGP<br>Hydrolyzed Wheat Glutan | 0.5 | 0.5 | 0.5 | — | — | — | — | 0.5 | — | — |
| Gluadin ® WK<br>Sodium Cocoyl Hydrolyzed Wheat Protein | 2.0 | 2.0 | 2.0 | 2.0 | 5.0 | — | — | — | 0.5 | 0.5 |
| Euperlan ® PK 3000 AM<br>Glycol Distearate (and) Laureth-4 (and)<br>Cocamidopropyl Betaine | 5.0 | — | — | 5.0 | — | — | — | — | — | — |
| Highcareen ® GS<br>Betaglucan | 1.0 | 1.0 | 1.0 | 1.0 | 1.0 | 1.0 | 1.0 | 1.0 | 1.0 | 1.0 |
| Hydagen ® CMF<br>Chitosan | 1.0 | 1.0 | 1.0 | 1.0 | 1.0 | 1.0 | 1.0 | 1.0 | 1.0 | 1.0 |
| Magnesium Sulfate Hepta Hydrate | — | — | — | — | — | — | — | — | 1.0 | 1.0 |
| Glycerin (85% by weight) | — | — | — | — | — | 3.0 | 3.0 | 5.0 | 5.0 | 3.0 |

What is claimed is:

1. A process for the production of branched, substantially unsaturated fatty alcohol ether sulfates comprising the steps of: (a) dimerizing an unsaturated $C_{16-22}$ fatty acid to form a dimer fraction and a monomer fraction comprised of branched, substantially unsaturated fatty acids and straight chain saturated fatty acids, (b) separating the monomer fraction from the dimer fraction, (c) converting the branched, substantially unsaturated fatty acids in the monomer fraction into the corresponding fatty acid methyl esters, (d) hydrogenating the branched, substantially unsaturated fatty acid methyl esters with the double bonds intact to form the corresponding branched, substantially unsaturated fatty alcohols and (e) sulfating and neutralizing the branched, substantially unsaturated fatty alcohols.

2. The process of claim 1 wherein the branched, substantially unsaturated fatty alcohols are sulfated with sulfur trioxide or chlorosulfonic acid.

3. The process of claim 1 wherein step (e) is carried out in a falling-film reactor.

4. The process of claim 1 wherein step (e) is carried out at temperature of from about 25 to about 90° C.

5. The process of claim 1 wherein in step (e) the molar ratio of fatty alcohol to sulfating agent is from about 1:0.95 to about 1:1.8.

6. The process of claim 1 wherein the methyl esters and/or the corresponding branched, substantially unsaturated fatty alcohols are distilled prior to step (e).

* * * * *